United States Patent [19]

Symon

[11] 4,304,939

[45] Dec. 8, 1981

[54] PREPARATION OF N-PHENYL-N-ALKYLPHENYLENEDIAMINES

[75] Inventor: Ted Symon, Lombard, Ill.

[73] Assignee: UOP Inc., Des Plaines, Ill.

[21] Appl. No.: 957,263

[22] Filed: Nov. 2, 1978

[51] Int. Cl.³ ............................................... C07C 85/08
[52] U.S. Cl. .................................... 564/396; 564/397; 564/398
[58] Field of Search ................ 260/576, 577, 581, 582; 564/396, 397, 398

[56] References Cited

U.S. PATENT DOCUMENTS

| 2,809,994 | 10/1957 | Hinckley | 260/574 |
| 4,140,718 | 2/1979 | Symon | 260/576 |
| 4,155,936 | 5/1979 | Sturm | 260/576 |

OTHER PUBLICATIONS

Morrison et al., "Organic Chemistry", 2nd Edition, p. 492 (1966).

*Primary Examiner*—John Doll
*Attorney, Agent, or Firm*—James R. Hoatson, Jr.; Raymond H. Nelson; William H. Page, II

[57] ABSTRACT

The desired compounds, namely, N-phenyl-N'-alkylphenylenediamines, are prepared by the reductive alkylation of a nitrogen-containing diphenylamine and a ketone in the presence of hydrogen and a hydrogenation catalyst. The desired product may be obtained in a more economical way when effecting the process in a continuous manner by utilizing an organic solvent for the reaction which comprises an ether compound such as a monoether of a dihydric alcohol, a diether of a dihydric alcohol, or a cyclic diether.

14 Claims, No Drawings

PREPARATION OF N-PHENYL-N-ALKYLPHENYLENEDIAMINES

BACKGROUND OF THE INVENTION

Certain compounds such as N-phenyl-N'-alkylphenylenediamines which are prepared by the reductive alkylation of a nitrogen-containing diphenylamine and a ketone in the presence of hydrogen and a suitable hydrogenation catalyst are utilized as additives for petroleum products such as gasoline in which the compounds which are added to the petroleum product act as an antioxidant and as an inhibitor sweetening agent. The reaction for preparing the desired unsymmetrical phenylenediamines may be effected under high pressure when utilizing either a batch or continuous type of operation. For example, when utilizing a batch type process, the solid diphenylamine possessing a substituent containing a nitrogen atom is poured into the reactor along with the catalyst, following which the ketone and the solvent are then added. The reactor is sealed, pressured with hydrogen and heated to the desired operating temperature while subjecting the mixture to continuous agitation such as by stirring. The resultant product, which may comprise either a liquid or a low melting solid, is filtered to free the same from the catalyst, following which the solvent may then be removed by distillation.

When effecting the reductive alkylation process in a continuous manner, the reactants must, of necessity, be in solution in order that they may be continuously pumped into a reactor containing the catalyst and heated under hydrogen pressure. However, some difficulty is encountered when utilizing a continuous process inasmuch as p-nitrodiphenylamine has a poor solubility in most organic solvents. For example, it is almost insoluble in aliphatic hydrocarbons, only slightly soluble in aromatic hydrocarbons, and has a limited solubility in esters, alcohols and ketones. When utilizing a high molecular weight ketone as the alkylating agent, it has been found that excess ketone must be used as both the alkylating agent and solvent. However, the ketones which are used possess a particular disadvantage of being reduced to the corresponding alcohols and therefore it is necessary to dehydrogenate the alcohols back to the ketone. Likewise, when using low molecular weight ketones as alkylating agents, the ketones cannot be used in excess as a solvent due to the fact that they possess the facility of replacing both amine hydrogens of an aromatic amine, thereby forming undesirable dialkylated products.

The preparation of N-phenyl-N'-isopropyl-p-phenylenediamine, an effective gasoline antioxidant and inhibitor sweetening agent, may be used as an illustration of the problems which are encountered when preparing an N-phenyl-N'-alkylphenylenediamine. This compound is prepared by the reductive alkylation of p-nitrodiphenylamine with acetone. Inasmuch as, as hereinbefore set forth, p-nitrodiphenylamine has a limited solubility in ketones, it has been necessary to utilize a high mole ratio of acetone p-nitrodiphenylamine in the order of about 8:1 to about 10:1 in order to obtain a solution in which the p-nitrodiphenylamine is sufficiently solubilized in order that the solution is capable of being pumped into a continuous plant. However, stoichiometrically, only a 1:1 mole ratio is required. The use of such an excess of acetone will cause further reaction with the monoalkyl product to form unacceptable amounts of di-N-alkylated by-products and will result in the loss of both acetone and hydrogen in the reduction of acetone to alcohol. In addition, the excess acetone will also interfere with the separation of water in the solvent recovery system of the plant.

Some prior art references have shown reductive alkylation processes. For example, Canadian Pat. No. 862,797 discloses a reductive alkylation process in which a sulfided platinum catalyst is used for the reductive alkylation of an organic compound containing an amino and/or a nitro substituent. U.S. Pat. 2,969,394 is drawn to a combination process, one step of which involves the reductive alkylation of an aromatic amino or nitro compound with a ketone during which an alcohol is formed from the ketone and is converted back to the ketone for further use within the process. Another prior art patent, namely, U.S. Pat. No. 3,522,309 teaches the use of polar solvents such as a 5 to 20% of lower alcohols or hydrogenated hydrocarbons to increase the rate of the reductive alkylation reaction. However, the solvents which were utilized in this reference are not particularly effective as solvents for the particular diphenylamines which are used as one of the starting materials in the present process.

As will hereinafter be shown in greater detail, the process of the present invention avoids the use of excess ketone by utilizing certain organic solvents of the ether type to solubilize the diphenylamine compounds possessing a substituent which contains a nitrogen atom in the form of nitro, nitroso or amino radicals. By utilizing the particular solvents of the present invention, namely, certain mono and diethers of dihydric alcohols, it is possible to provide an economical plant throughput, the amount of ketone which is used in the reaction as an alkylating agent being reduced to slightly over the stoichiometric requirement. The advantages which are obtained by using these solvents are the avoidance of the formation of large quantities of alcohols due to the reduction of the ketone to the alcohol, the realization of a favorable reaction rate and the relatively simple recovery of the solvent from the reaction mass and separation from the water of reaction, thus rendering the solvents available for recycle. In addition, by utilizing almost stoichiometric amounts of ketone as the alkylating agent, it is possible to prevent the formation of over alkylated by-products in reactions where low molecular weight ketones are employed.

This invention relates to a process of the reductive alkylation of diphenylamines containing a nitro, nitroso or amino substituent with a ketone. More specifically, the invention is concerned with an improvement in the reductive alkylation process for preparing unsymmetrical N-phenyl-N'-alkylphenylenediamines whereby said process may be uneffected using relatively low mole ratios of alkylating agent to diphenylamine compounds.

As hereinbefore set forth the product which results from the process of the present invention, namely, N-phenyl-N'-alkylphenylenediamines may be utilized as additives for petroleum products such as gasoline, fuel oil, jet oil, heating oil, etc., whereby oxidation of the petroleum product with the corresponding formation of undesirable gums and tars will be prevented or retarded. In addition, these compounds will also act as inhibitor sweetening agents and as antioxidants in various types of rubbers.

It is therefore an object of this invention to provide an improved process for the preparation of unsymmetrical N-phenyl-N'-alkylphenylenediamines.

A further object of this invention is to provide an improvement in the process for the reductive alkylation of a nitrogen substituted diphenylamine with a ketone by utilizing a solvent which possesses a particular configuration.

In one aspect an embodiment of this invention resides in a process for the preparation of N-phenyl-N'-alkylphenylenediamine which comprises the reductive alkylation of a nitrogen-containing compound selected from the group consisting of nitrodiphenylamines, nitrosodiphenylamines, and aminodiphenylamines and a ketone in the presence of hydrogen and a hydrogenation catalyst at reaction conditions and recovering the resultant N-phenyl-N'-alkylphenylenediamine, the improvement which consists in effecting said process in the presence of an organic solvent comprising an ether selected from the group consisting of the monoethers of dihydric alcohols, the diethers of dihydric alcohols and cyclic ethers.

A specific embodiment of this invention is found in a process for preparing an N-phenyl-N'-alkylphenylenediamine which comprises reductively alkylating p-nitrodiphenylamine with acetone in the presence of hydrogen and a hydrogenation catalyst at a temperature in the range of from about 80° to about 240° C. and a pressure in the range of from about 2 to about 2000 psi in a solvent medium comprising 2-methoxyethanol, and recovering the resultant N-phenyl-N'-isopropyl-p-phenylenediamine.

Other objects and embodiments will be found in the following further detailed description of the present invention.

As hereinbefore set forth the present invention is concerned with an improvement in a process for the reductive alkylation of a diphenylamine possessing a nitrogen-containing substituent with a ketone, the improvement which comprises utilizing a particular type of solvent for the amine compound to be permitting the reaction to be effected in the presence of a lesser amount of the alkylating agent comprising a ketone. One advantage of utilizing this particular type of solvent for the reductive alkylation reaction is that the amine compound is sufficiently soluble in the aforesaid solvent so as to provide an economical plant throughput. In addition, the rate of reaction will also be favorably increased as well as the amount of alkylating agent which is utilized in the reaction can be reduced to slightly over stoichiometric amounts, thus avoiding the formation of large quantities of alcohols with a concomitant dehydrogenation to form the desired ketone again. Examples of ether compounds which may be employed as solvents for the reaction of the present invention will include monoethers of dihydric alcohols, diethers of dihydric alcohols, and cyclic diethers. Some representative examples of these ethers which may be employed will include monoethers of dihydric alcohols such as 2-methoxyethanol, 2-ethoxyethanol, 2-propoxyethanol, 1-methoxy-2-propanol, 2-methoxy-1-propanol, 1-ethoxy-2-propanol, 1-propoxy-2-propanol, 1methoxy-2-butanol, 2-methoxy-1-butanol, 1-ethoxy-2-butanol, 1-propoxy-2-butanol, diethyleneglycol monomethyl ether, diethyleneglycol monoethyl ether, diethyleneglycol monopropyl ether, triethyleneglycol monomethyl ether, triethyleneglycol monoethyl ether, dipropyleneglycol monomethyl ether, dipropyleneglycol monoethyl ether, tripropyleneglycol monomethyl ether, tripropyleneglycol monoethyl ether, etc.; the diethers of dihydric alcohols such as ethyleneglycol dimethyl ether, ethyleneglycol diethyl ether, ethyleneglycol dipropyl ether, diethyleneglycol dimethyl ether, diethyleneglycol diethyl ether, diethyleneglycol dipropyl ether, propyleneglycol dimethyl ether, propyleneglycol diethyl ether, propyleneglycol dipropyl ether, dipropyleneglycol dimethyl ether, dipropyleneglycol diethyl ether, dipropyleneglycol dipropyl ether, etc.; cyclic ethers such as 1,3-dioxane, 1,4-dioxane, etc. It is to be understood that the aforementioned ethers are only representative of the class of compounds which may be employed as solvents and that the present invention is not necessarily limited thereto.

Some specific examples of the amine compounds which are reductively alkylated according to the process of this invention will include p-nitrodiphenylamine, p-nitrosodiphenylamine, p-aminodiphenylamine, o-nitrodiphenylamine, o-aminodiphenylamine, diphenylamine compounds containing other substituents in addition to the nitrogen-containing substituent such as 2-methyl-4-nitrodiphenylamine, 2-ethyl-4-nitrodiphenylamine, 2-propyl-4-nitrodiphenylamine, 2-methoxy-4-nitrodiphenylamine, 2-ethoxy-4-nitrodiphenylamine, 2-propoxy-4-nitrodiphenylamine, 2-methyl-4-nitrosodiphenylamine, 2-ethyl-4-nitrosodiphenylamine, 2-propyl-4-nitrosodiphenylamine, 2-methoxy-4-nitrosodiphenylamine, 2-ethoxy-4-nitrosodiphenylamine, 2-propoxy-4-nitrosodiphenylamine, 2-methyl-4-aminodiphenylamine, 2ethyl-4-aminodiphenylamine, 2-propyl-4-aminodiphenylamine, 2-methoxy-4-aminodiphenylamine, 2-ethoxy-4-aminodiphenylamine, 2-propoxy-4-aminodiphenylamine, 4-methyl-2-nitrodiphenylamine, 4-ethyl-2-nitrodiphenylamine, 4-propyl-2-nitrodiphenylamine, 4-methoxy-2-nitrodiphenylamine, 4-ethoxy-2-nitrodiphenylamine, 4-propoxy-2-nitrodiphenylamine, 4-methyl-2-aminodiphenylamine, 4-ethyl-2-aminodiphenylamine, 4-propyl-2-aminodiphenylamine, 4-methoxy-2-aminodiphenylamine, 4-ethoxy-2-aminodiphenylamine, 4-propoxy-2-aminodiphenylamine, 2-methyl-4'-nitrodiphenylamine, 2-ethyl-4'-nitrodiphenylamine, 2-methoxy-4'-nitrodiphenylamine, 2-ethoxy-4'-nitrodiphenylamine, 2-methyl-4'-aminodiphenylamine, 2-ethyl-4'aminodiphenylamine, 2-methoxy-4'-aminodiphenylamine, 2-ethoxy-4'-aminodiphenylamine, 4-methyl-4'-nitrodiphenylamine, 4-ethyl-4'nitrodiphenylamine, 4-methoxy-4'-nitrodiphenylamine, 4-ethyl-4'-nitrosodiphenylamine, 4-methoxy-4'-nitrosodiphenylamine, 4-ethoxy-4'-nitrodiphenylamine, 4-methyl-4'-aminodiphenylamine, 4-ethyl-4'-aminodiphenylamine, 4-methoxy-4'-aminodiphenylamine, 4-ethoxy-4'-aminodiphenylamine, etc. It is to be understood that the aforementioned compounds are only representative of the class of reactants which may be employed, and that the present invention is not necessarily limited thereto.

Examples of ketones which may be employed as alkylating agents in the reductive alkylation process of the present invention will include aliphatic ketones such as acetone, methyl ethyl ketone, diethyl ketone, methyl propyl ketone, methyl butyl ketone, methyl amyl ketone, methyl hexyl ketone, methyl heptyl ketone, methyl octyl ketone, methyl decyl ketone, ethyl propyl ketone, ethyl butyl ketone, ethyl amyl ketone, ethyl hexyl ketone, ethyl heptyl ketone, ethyl octyl ketone, ethyl nonyl ketone, dipropyl ketone, propyl butyl ketone, propyl amyl ketone, propyl hexyl ketone, propyl heptyl ketone, dibutyl ketone, the alkyl chains being either straight or branched chained in configuration, etc.; cycloaliphatic ketones such as cyclobutanone, cyclopentanone, cyclohexanone, cycloheptanone, cyclooctanone, etc.

The reductive alkylation of the diphenylamine possessing a substituent containing a nitrogen atom with a ketone is effected by charging the diphenylamine compound along with a ketone and the solvent to an appropriate apparatus which contains a hydrogenation catalyst. The term "reductive alkylation" as used in the present specification and appended claims will refer to the use of both aliphatic and cycloaliphatic alkylating agents. The hydrogenation catalyst which is to be employed in the reductive alkylation process can be chosen from any of those well known in the art, such catalysts including nickel, platinum composited on a solid support such as alumina, platinum composited on carbon, platinum composited on a diatomaceous earth, palladium composited on alumina, palladium composited on carbon, palladium composited on a diatomaceous earth, etc. Following the introduction of the reactants into the reaction apparatus such as an autoclave, the apparatus is sealed and pressured to the desired operating pressure with hydrogen, said pressure ranging from about 2 to about 2000 pounds per square inch (psi). Following this, the reaction mixture is thoroughly admixed by mechanical means such as stirrers or by rocking, rotating, etc., and heated to the desired operating temperature which is in a range of from about 80° to about 240° C. Inasmuch as the reaction is exothermic in nature, due to the rapid reduction of the nitro groups, if the nitrogen-containing substituent is nitro or nitroso, hydrogen will be rapidly consumed. Therefore, it is necessary to maintain the desired operating pressure and an additional amount of hydrogen. At the end of the predetermined residence time, heating may be discontinued and the reaction mixture can be recovered from the apparatus after the apparatus has been allowed to return to room temperature and the excess pressure vented. The desired product comprising an unsymmetric N-phenyl-N'-alkylphenylenediamine is separated from any unreacted starting materials and/or by-products by conventional means such as washing, drying, fractional distillation, etc., and recovered.

As hereinbefore set forth by utilizing solvent of the particular type of the present invention, it is possible to effect the reductive alkylation process in a continuous manner of operation. When this type of operation is employed, the reactants comprising the diphenylamine compound which is dissolved in an appropriate solvent of the type hereinbefore set forth in greater detail and the ketone are continuously charged to a reactor which is maintained at the proper operating conditions of temperature and pressure and which contains a hydrogenation catalyst. In addition, hydrogen is also continuously charged to the reactor and upon completion of the desired residence time in the reactor the effluent is continuously withdrawn and subjected to conventional means of separation whereby the N-phenyl-N'-alkylphenylenediamine is separated from any unreacted starting materials and recovered, the unreacted starting materials being recycled to the reactor to form a portion of the feed stock.

Some examples of N-phenyl-N'-alkylphenylenediamines which may be prepared according to the process of this invention will include N-phenyl-N'-isopropyl-p-phenylenediamine, N-phenyl-N'-sec-butyl-p-phenylenediamine, N-phenyl-N'-sec-pentyl-p-phenylenediamine, N-phenyl-N'-sec-hexyl-p-phenylenediamine, N-phenyl-N'-sec-heptyl-p-phenylenediamine, N-phenyl-N'-sec-octyl-p-phenylenediamine, N-phenyl-N'-sec-nonyl-p-phenylenediamine, N-phenyl-N'-sec-decyl-p-phenylenediamine, N-phenyl-N'-sec-undecyl-p-phenylenediamine, N-phenyl-N'-cyclopentyl-p-phenylenediamine, N-phenyl-N'-cyclohexyl-p-phenylenediamine, N-phenyl-N'-cycloheptyl-p-phenylenediamine, N-phenyl-N'-isopropyl-o-phenylenediamine, N-phenyl-N'-sec-butyl-o-phenylenediamine, N-phenyl-N'-sec-pentyl-o-phenylenediamine, N-phenyl-N'-sec-hexyl-o-phenylenediamine, N-phenyl-N'-sec-heptyl-o-phenylenediamine, N-phenyl-N'-sec-octyl-o-phenylenediamine, N-phenyl-N'-sec-nonyl-o-phenylenediamine, N-phenyl-N'-sec-decyl-o-phenylenediamine, N-phenyl-N'-sec-undecyl-o-phenylenediamine, N-phenyl-N'-cyclopentyl-o-phenylenediamine, N-phenyl-N'-cyclohexyl-o-phenylenediamine, N-phenyl-N'-cycloheptyl-o-phenylenediamine, etc.

The following examples are given to illustrate the process of the present invention. However, it is to be understood that these examples are given merely for purposes of illustration and that the present invention is not necessarily limited thereto.

EXAMPLE I

A charge consisting of 0.5 moles of p-nitrodiphenylamine, 0.6 moles of acetone and 150 grams of 2-methoxyethanol may be added to a magnetically stirred 1 liter stainless steel autoclave which is equipped with a hydrogen charging system, a sampling dip-leg, a heater, a thermocouple well and a water cooling coil, said autoclave containing 12 grams of a hydrogenation catalyst comprising platinum on alumina. After charging the autoclave with the starting materials, the apparatus may then be sealed, flushed with hydrogen, and pressured to about 1000 psig with hydrogen. Thereafter the mixture may be stirred and heated to a temperature of 140° C., hydrogen being added thereto in incremental portions in order to maintain the aforesaid pressure. After a period of about 5 hours, the heating may be discontinued and the autoclave allowed to return to room temperature. After discharging the excess pressure the autoclave may be opened and the reaction mixture recovered therefrom. This mixture may then be subjected to gas liquid chromatographic analysis to determine the presence of a major portion of N-phenyl-N'-isopropyl-p-phenylenediamine with relatively minor portions of the diisopropyl product.

EXAMPLE II

In like manner a charge consisting of 0.5 mole of p-nitrosodiphenylamine, 0.6 mole of methyl ethyl ketone, and 100 grams of 1-methoxy-2-propanol may be charged to an autoclave containing 12 grams of a platinum on alumina hydrogenation catalyst. As in the above example, the autoclave may be sealed, flushed with hydrogen and pressured to about 1000 psig. The mixture may be thoroughly stirred and heated to a temperature of about 40° C. to effect the reduction of the nitroso group to the amine. Thereafter the reaction mixture is heated to about 160° C. to complete the reductive alkylation. The autoclave and contents thereof may be maintained at this temperature for a reaction period of about 5 hours, hydrogen being replaced periodically in order to maintain the desired operating pressure. At the end of the 5 hour period heating may be discontinued and the autoclave allowed to return to room temperature. After discharge of the excess pressure the autoclave may be opened and the reaction mixture recovered therefrom. The mixture may then be subjected to gas liquid chromatographic analysis to determine the presence of a major portion of the desired product comprising N-phenyl-N'-sec-butyl-p-phenylenediamine with only a relatively minor amount of the di-sec-butyl product being present.

EXAMPLE III

In this example a charge consisting of p-aminodiphenylamine with a slight excess of methyl hexyl ketone and a solvent comprising 150 grams of diethyleneglycol dimethyl ether as a solvent may be placed in an autoclave along with 15 grams of a nickel hydrogenation catalyst. The autoclave after sealing may be flushed with hydrogen and thereafter pressured to an initial operating pressure of about 1000 psig. After reaching the desired operating pressure, the autoclave may be heated to a temperature of about 140° C. and maintained thereat for a period of about 5 hours, additional hydrogen being charged thereto in incremental portions in order to maintain the desired operating pressure. At the end of the 5 hour period the autoclave and contents thereof are treated in a manner similar to that hereinbefore set forth, the gas liquid chromatographic anaylsis being used to determine the presence of the desired N-phenyl-N'-sec-octyl-p-phenylenediamine.

EXAMPLE IV

To a magnetically stirred autoclave may be charged a mixture consisting of 0.5 mole of o-nitrodiphenylamine, 0.55 mole of cyclohexanone and 250 grams of a solvent comprising 2-methoxyethanol. The autoclave which contains a hydrogenation catalyst comprising platinum composited on alumina may then be sealed and flushed with hydrogen. After pressuring the autoclave to about 1000 psig with hydrogen the mixture may be stirred and heated to a temperature of about 120° C. In order to maintain the desired operating pressure, hydrogen may be added in incremental portions during the reaction period of 5 hours, at the end of the 5 hour period heating is discontinued and the autoclave is allowed to return to room temperature and the excess pressure may be vented. After opening the autoclave and recovering the reaction mixture therefrom, the mixture may be subjected to gas liquid chromatographic analysis to determine the presence of a major portion of the desired product comprising N-phenyl-N'-cyclohexyl-o-phenylenediamine.

EXAMPLE V

In this example a charge consisting of 0.5 mole of o-aminodiphenylamine, 0.55 mole of ethyl octyl ketone and 250 grams of diethyleneglycol diethyl ether along with 15 grams of a nickel hydrogenation catalyst may be placed in an autoclave provided with magnetic stirring means. The autoclave may be sealed, flushed with hydrogen and pressured to an initial operating pressure of 1000 psig with hydrogen. After reaching the desired operating pressure the mixture may be stirred and heated to a temperature of about 150° C., said temperature being maintained for a period of about 5 hours. In addition, to compensate for any pressure drop which may occur, hydrogen may be added incrementally during the reaction period. At the end of the 5 hour reaction time, heating may be discontinued and the autoclave allowed to return to room temperature. After discharging the excess pressure the autoclave may be opened, the reaction mixture recovered therefrom, and subjected to gas liquid chromatographic analysis to determine the presence of a major portion of the desired product comprising N-phenyl-N'-sec-undecyl-o-phenylenediamine.

I claim as my invention:

1. In a process for the continuous preparation of N-phenyl-N'-alkylphenylenediamine which comprises the reductive alkylation of a nitrogen-containing compound selected from the group consisting of nitrodiphenylamines, nitrosodiphenylamines, and aminodiphenylamines with a ketone in the presence of hydrogen and a hydrogenation catalyst consisting essentially of a Group VIII metal selected from the group consisting essentially of nickel, platinum, and palladium dispersed on a solid support at reaction conditions and recovering the resultant N-phenyl-N'-alkylphenylenediamine, the improvement which consists in effecting said process in the presence of a protic organic solvent consisting essentially of a monoether of a dihydric alcohol.

2. The process as set forth in claim 1 in which said reaction conditions include a temperature in the range of from about 80° to about 240° C. and a pressure in the range of from about 2 to about 2000 pounds per square inch.

3. The process as set forth in claim 1 in which said ketone is acetone.

4. The process as set forth in claim 1 in which said ketone is methyl ethyl ketone.

5. The process as set forth in claim 1 in which said ketone is methyl hexyl ketone.

6. The process as set forth in claim 1 in which said ketone is cyclohexanone.

7. The process as set forth in claim 1 in which said ketone is ethyl octyl ketone.

8. The process as set forth in claim 1 in which said protic organic solvent ether is 2-methoxyethanol.

9. The process as set forth in claim 1 in which said protic organic solvent ether is 1-methoxy-2-propanol.

10. The process as set forth in claim 1 in which said nitrogen-containing compound is p-nitrodiphenylamine, said ketone is acetone and said N-phenyl-N'-alkylphenylenediamine is N-phenyl-N'-isopropyl-p-phenylenediamine.

11. The process as set forth in claim 1 in which said nitrogen-containing compound is p-nitrosodiphenylamine, said ketone is methyl ethyl ketone, and said N-phenyl-N'-alkylphenylenediamine is N-phenyl-N'-sec-butyl-p-phenylenediamine.

12. The process as set forth in claim 1 in which said nitrogen-containing compound is p-aminodiphenylamine, said ketone is methyl hexyl ketone and said N-phenyl-N'-alkylphenylenediamine is N-phenyl-N'-sec-octyl-p-phenylenediamine.

13. The process as set forth in claim 1 in which said nitrogen-containing compound is o-nitrodiphenylamine, said ketone is cyclohexanone and said N-phenyl-N'-alkylphenylenediamine is N-phenyl-N'-cyclohexyl-o-phenylenediamine.

14. The process as set forth in claim 1 in which said nitrogen-containing compound is o-aminodiphenylamine, said ketone is ethyl octyl ketone and said N-phenyl-N'-alkylphenylenediamine is N-phenyl-N'-sec-undecyl-o-phenylenediamine.

* * * * *